(12) United States Patent
Lindauer et al.

(10) Patent No.: US 6,838,033 B2
(45) Date of Patent: Jan. 4, 2005

(54) DECORATIVE MATERIALS ENCASED IN A POLYMER WITH FRAGRANCE RELEASING CHARACTERISTICS

(75) Inventors: Jerome I. Lindauer, Hillsdale, NJ (US); Robert Reid, Brick, NJ (US); Lynn Iarossi, Long Branch, NJ (US); Andrea Lynn Meyer, Middletown, NJ (US)

(73) Assignee: International Flavors and Fragrances Inc., New York, NY (US)

( * ) Notice: Subject to any disclaimer, the term of this patent is extended or adjusted under 35 U.S.C. 154(b) by 589 days.

(21) Appl. No.: 09/947,639

(22) Filed: Sep. 6, 2001

(65) Prior Publication Data

US 2002/0015808 A1 Feb. 7, 2002

Related U.S. Application Data

(62) Division of application No. 09/630,728, filed on Aug. 2, 2000, now Pat. No. 6,309,715.

(51) Int. Cl.⁷ .............................................. B29C 39/10
(52) U.S. Cl. ...................... 264/247; 264/275; 264/279; 264/279.1; 425/DIG. 57
(58) Field of Search ................ 264/275, 279, 264/279.1, 247; 425/DIG. 57

(56) References Cited

U.S. PATENT DOCUMENTS

| | | | |
|---|---|---|---|
| 4,411,855 A | * 10/1983 | Fiebig et al. | ............... 264/219 |
| 4,476,171 A | * 10/1984 | Takeuchi | ..................... 428/38 |
| 4,500,725 A | 2/1985 | Yemoto et al. | |
| 4,504,433 A | * 3/1985 | Inui et al. | ................... 510/146 |
| 4,524,018 A | 6/1985 | Yemoto, II et al. | |
| 4,552,693 A | 11/1985 | Hussain et al. | |
| 4,908,208 A | 3/1990 | Lee et al. | |
| 5,008,115 A | 4/1991 | Lee, II et al. | |
| 5,071,704 A | 12/1991 | Fischel-Ghodsian | |
| 5,130,171 A | 7/1992 | Prud'Homme et al. | |
| 5,176,903 A | 1/1993 | Goldberg et al. | |
| 5,185,155 A | 2/1993 | Behan et al. | |
| 5,234,689 A | 8/1993 | Lindauer et al. | |
| 5,324,444 A | 6/1994 | Berry et al. | |
| 5,372,806 A | 12/1994 | Holloway | |
| 5,387,411 A | 2/1995 | Abrutyn et al. | |
| 5,387,622 A | 2/1995 | Yamamoto | |
| 5,490,982 A | 2/1996 | Siciliano | |
| 5,500,223 A | 3/1996 | Behan, II et al. | |
| 5,525,555 A | 6/1996 | Zank | |
| 5,525,588 A | 6/1996 | Michetti | |
| 5,578,089 A | 11/1996 | Elsamaloty | |
| 5,679,334 A | 10/1997 | Semoff et al. | |
| 5,783,657 A | 7/1998 | Pavlin et al. | |
| 5,843,194 A | 12/1998 | Spaulding | |
| 5,871,765 A | 2/1999 | Johnson et al. | |
| 5,964,905 A | 10/1999 | Camp et al. | |
| 5,998,570 A | 12/1999 | Pavlin, II et al. | |
| 6,033,210 A | 3/2000 | Freeman | |
| 6,054,547 A | 4/2000 | Perry et al. | |
| 6,066,328 A | 5/2000 | Ribier et al. | |
| 6,111,055 A | 8/2000 | Berger et al. | |
| 6,214,063 B1 | 4/2001 | DeStefano et al. | |

FOREIGN PATENT DOCUMENTS

JP           09053098 A   *   2/1997

* cited by examiner

Primary Examiner—Edmund H. Lee
(74) Attorney, Agent, or Firm—Joseph F. Leightner

(57) ABSTRACT

The present invention provides a fragrant article that delivers fragrance over a period of time by an article comprising a polymer matrix, a fragrance and a decorative object. The decorative object is contained within a polymer matrix and in a preferred embodiment is the similar to the fragrance that is being released. The article is particularly well suited to be used as a room freshener, which because of its attractive appearance does not need to be hidden.

6 Claims, 2 Drawing Sheets

DECORATIVE MATERIALS ENCASED IN A POLYMER WITH FRAGRANCE RELEASING CHARACTERISTICS

STATUS OF RELATED APPLICATIONS

This application is a divisional application, of U.S. Ser. No. 09/630,728, filed on Aug. 2, 2000 now U.S. Pat. No. 6,309,715, the contents hereby incorporated by reference as if set forth in its entirety.

FIELD OF THE INVENTION

The present invention relates to polymeric materials containing a decorative item, the polymeric material is also capable of releasing a fragrance. In a preferred embodiment of the invention the decorative item and the fragrance which is emitted from the polymeric material are related.

BACKGROUND OF THE INVENTION

The release of fragrance to mask malodor or to provide a pleasant surrounding is desirable in various applications. Room deodorizers can be applied by aerosol means, but suffer from the deficiency of needing repeated applications. Consequently, solid room deodorizers have been developed, but unfortunately the object have been relatively unsightly. Consequently, the room deodorizers have been relegated to areas such as under sinks, behind doors or inside of closets. It would be highly desirable to create attractive articles that would release fragrances to create pleasant environments The slow sustained release of a fragrant molecule is a desirable trait in various applications including personal care products, air fresheners and the like. Among the suitable techniques for providing long lasting scents are dissolving or suspending fragrance compounds in emulsions (see U.S. Pat. Nos. 5,525,588; 5,525,555; 5,490,982 and 5,372,806); encapsulation of a fragrance (U.S. Pat. Nos. 5,500,223; 5,324,444, 5,185,155, 5,176,903 and 5,130,171); dissolving a fragrance into a hydrophilic phase such as silicone U.S. Pat. No. 5,234,689) incorporation of a fragrance into a cross-liked polymer (U.S. Pat. Nos. 5,387,622 and 5,387,411) incorporation of a fragrance into permanent laminates (U.S. Pat. Nos. 5,071,704 and 5,008,115) incorporation of a fragrance that softens at body temperature (U.S. Pat. No. 4,908,208) incorporation of a fragrance into silanes with fragrant alcohol to form alkoxysilanes (U.S. Pat. Nos. 4,524,018 and 4,500,725 incorporation of fragrant moieties via hydrosilation of an olefinic silane molecule (U.S. Pat. No. 6,054,547). The disclosure of the above US patents are hereby incorporated by reference as if set forth in their entirety.

While all of these approaches release fragrant molecules, there is a continuing need to provide attractive dispensing means from which the fragrant molecules can be delivered.

SUMMARY OF THE INVENTION

The present invention provides an attractive item which can be prominently displayed and which also releases fragrance into the surrounding environment. In a first embodiment of the present invention provides a decorative item, a polymer matrix and fragrance wherein the decorative item is encased in the polymer matrix and a fragrance is emitted from the polymer.

In a second embodiment of the invention comprises a method for making the a decorative item encased in a polymer matrix comprising:

providing a monomer; a fragrance; and a catalyst suitable for the monomer;

admixing the monomer, fragrance and a catalyst;

providing a mold, said mold containing a decorative item;

providing the fragrance, monomer and catalyst mixture to the mold;

allowing the catalyst to polymerize the monomer mixture in the mold;

removing the decorative item encased in a fragrant polymer.

The present invention is suitable for use as an air freshener, an environmental fragrancing device and other applications. These and other embodiments of the present invention will become apparent upon referring to the following figure and description of the invention.

DETAILED DESCRIPTION OF THE INVENTION

Figure 1:
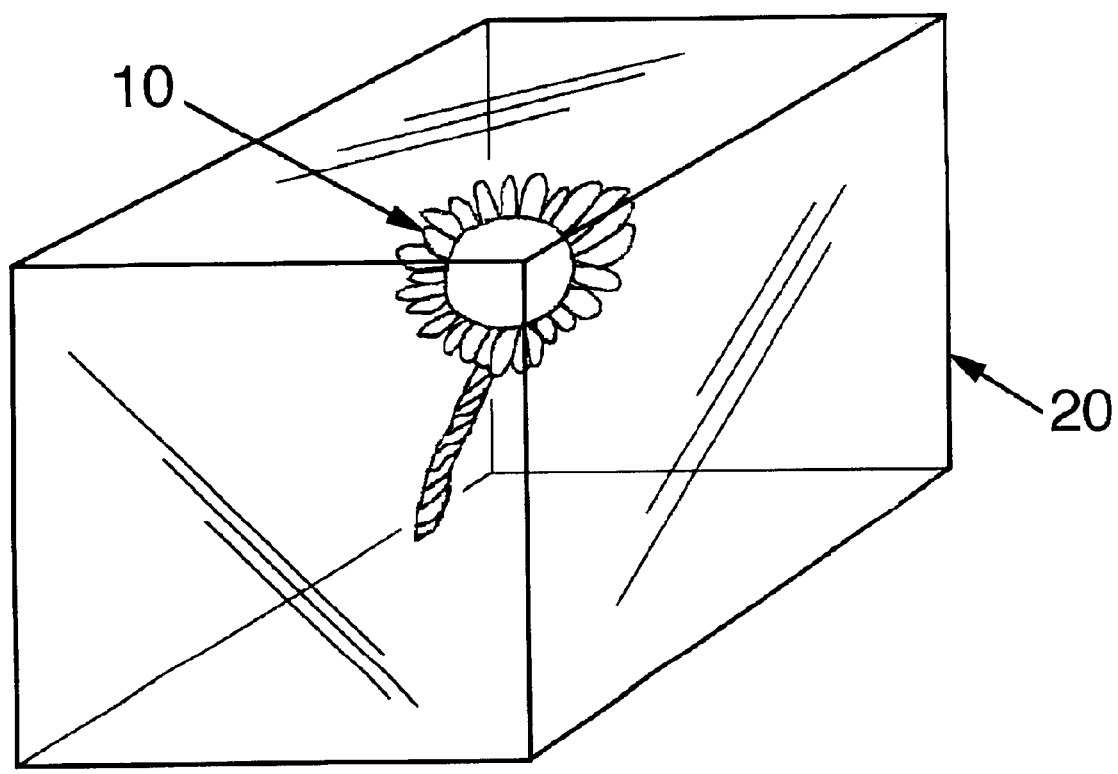
FIG. 1 is a plan view of a flower contained in a polymeric matrix in accordance with the present invention.

The polymer materials that are employed in the preset invention are selected from any material that will accept a fragrance material and which are transparent when used to encapsulate the decorative material. As used herein, essentially transparent is understood to mean the ability to transmit light without appreciable scattering so that bodies lying beyond the polymer material are visible. More preferably, the polymeric materials that are used are of sufficient clarity so that the decorative item is visible when it is encased in the polymeric material. Suitable polymers include, but are not limited to siloxanes, silicones, acrylics, polycarbonates, polyesters such as polyester terephthalate, copolymers and mixtures of these polymers and the like. The most preferred materials are siloxanes such as polydimethylsiloxanes, especially when catalyzed with an organotin compound and zinc silicate in the presence of a base. This polymethylsiloxane material was found to possess excellent optical properties, good structural properties as well as can be used to deliver fragrance over a period of time.

Structural properties are understood to mean the ability to remain rigid after being cast into a shape. Rigid is understood to mean that the polymer matrix will retain its shape after being removed from a mold and will not run, or sag. Some polymers are not very suitable in that they are too soft and will not retain the desired shape over time. Other polymers are undesirably soft in that the object feels mushy when handled. Other polymers are easily deformed when handled, acting similarly to putty materials. In a preferred embodiment, the polymer should appear like glass when initially viewed. In a highly preferred embodiment the polymer should also be capable of delivering a fragrance over an extended period of time.

The polymer is typically provided in an amount of greater than about 50 weight percent of the item, preferably greater than 70 weight percent and in a preferred embodiment greater than about 80 weight percent of the item.

The fragrance employed in the invention is not critical, so long as it is compatible with the polymer that is employed. As is appreciated in the art, some polymer and fragrances are not compatible with each other, that means that a particular fragrance can not be delivered with a specific polymer. The fragrance of the present invention can preferably be continually delivered over time such as more than a week, more than two weeks, preferably more than a month and most preferably over a period two or more months. Technologies for the control release of fragrances are well known in the art and include encapsulation, use of emulsions and surfactants and other techniques as set forth above.

Many types of fragrances can be employed in the present invention, the only limitation being the compatibility with the polymer matrix being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal scents such as and woodland scents derived from pine, spruce and other forest smells. Fragrances may also be derived from various oils, such as essential oils, or from plant materials such as peppermint, spearmint and the like. Other familiar and popular smells can also be employed such as baby powder, popcorn, pizza, cotton candy and the like can also be employed in the present invention.

A list of suitable fragrances is provided in U.S. Pat. No. 4,534,891, the contents of which are hereby incorporated by reference. Another source of suitable fragrances is found in *Perfumes Cosmetics and Soaps*, Second Edition, edited by W. A. Poucher, 1959. Among the fragrances provided in this treatise are acacia, cassie, chypre, cylamen, fern, gardenia, hawthorn, heliotrope, honeysuckle, hyacinth, jasmin, lilac, lily, magnolia, mimosa, narcissus, freshly-cut hay, orange blossum, orchids, reseda, sweet pea, trefle, tuberose, vanilla, violet, wallflower, and the like.

The level of fragrance varies from about 0.1 to about 10 weight percent, preferably from about 2 to about 8 and most preferably from about 3 to about 7 weight percent. In addition to the fragrance other agents can be used in conjunction with the fragrance. Well known materials such as surfactants, emulsifiers, polymers to encapsulate the fragrance can also be employed without departing from the scope of the present invention.

Also included in the present invention is a decorative item that is encased into the polymer matrix. Any decorative item can be included in the polymer, including but not limited to plant materials such as flowers, leaves, branches and twigs. Suitable materials include roses, lilac blooms, carnations and the like. Miniature items as models of cars, planes, and trains; miniature replicas of animals, including a stuffed animal such as a teddy bear, toys, cartoon figures, action figures, and the like can also be included in the polymeric matrix. The use of a child's favorite toy in the polymer matrix would be ideal for use in a child's room. Encased in the polymer matrix is understood that the decorative article is surrounded in three dimensions by the polymer. The present invention is not contemplated as including the placing of a decorative item on top of a polymer matrix.

In a highly preferred embodiment of the present invention, the item embedded in the polymer matrix and the fragrance incorporated into the polymer is the same. This provides a visual clue as to the scent when the person who may enter an area views it. Once a person notes the item, the person will associate the fragrance in the area with the item inside the polymer matrix.

The decorative items of the present invention are particularly well suited to be employed as room fresheners. Since the item has a pleasant appearance, it is not necessary to place the item out of sight. In fact, because the polymer matrix preserves the decorative item, the present invention makes it highly desirable to have the item in a visible place.

Now referring to the Figures, in FIG. 1 an embodiment of the invention is presented. The polymer matrix 10 is visible as well as the decorative item. In FIG. 1, a flower 10, more specifically a daisy, is employed as the decorative item in the polymer 20. A fragrance (not shown) is provided in the polymer matrix.

Figure 2:
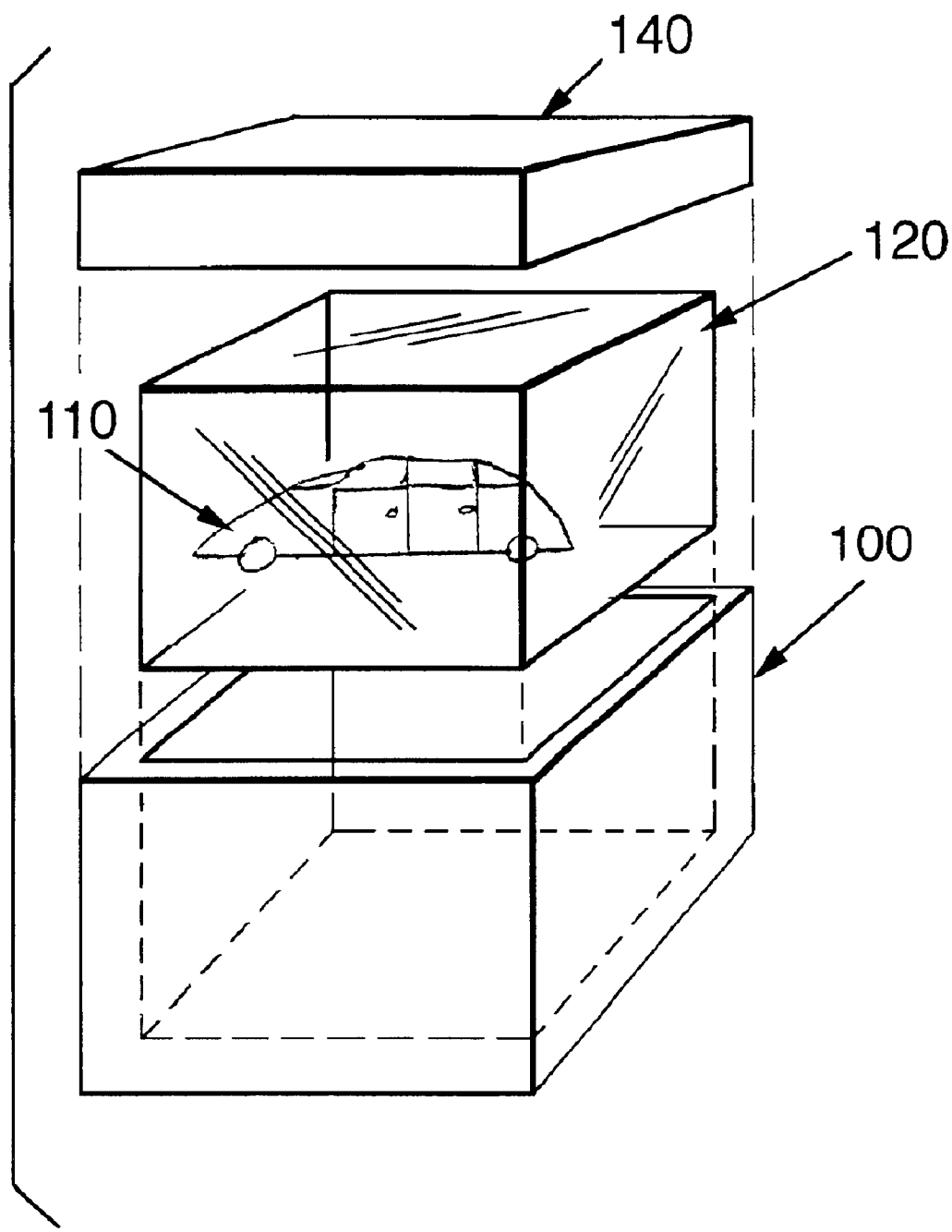
FIG. 2 is an exploded view of the present invention and an accompanying protective case.

In FIG. 2 an explode view of the polymer matrix, decorative item and a container is visible. The polymer matrix 120 containing the decorative item 110, the model car is visible, just above the container 100. The container in a preferred embodiment also has a lid 140 which can be employed to retain the fragrance within the polymer matrix when it is not desired.

The use of a container is not required in the present invention but has several advantages. First the container provides protection to the polymer and decorative item during shipping and display prior to purchase. In addition, the container also acts to prevent diminution of the fragrance prior to purchase and use. The container can be made of various materials, including cardboard, papers and films and the like. It is preferred that the package retards the release of fragrance before use. Films, including shrink-wrap films, used in food packaging would be useful especially if the film limits or prevents air mobility across the film. Suitable films include polymers and copolymers containing polyethylene, polypropylene and vinylidene chloride, which are known in the art.

Preferably the container is also made of a transparent material such as glass, acrylics, polycarbonates and the like. If the container is transparent the article can remain in the container and the top removed only when fragrance is desired.

As polymers are employed in the present invention, it is possible to make many different shapes and sizes in which to encase the decorative item. Cubes are a preferred shape inasmuch as they are generally considered to be appealing to the eye. Cubes are understood to include cube-like shapes that generally have sides that are similar in dimension, however they are not all required to have the exact same dimension. However, one with skill in the art will be able to cast polymers in a wide number of three-dimensional shapes such as spheres, ellipses, pyramids, parrellelpipeds, and the like.

These and additional modifications and improvements of the present invention may also be apparent to those with ordinary skill in the art. The particular combinations of element described and illustrated herein are intended only to represent only a certain embodiment of the present inventions and is not intended to serve as limitations of alternative articles with the spirit and scope of the invention.

EXAMPLE

A decorative rose encased in a polysiloxane matrix was prepared using the following method. One hundred (100) parts by weight of a siloxane (TBT4750 available from Path Silicones, Elmwood Park, N.J.) and 5 weight percent rose fragrance from International Flavor and Fragrance Inc. were mixed until a clear uniform solution is formed. To the clear mixture, 10 parts by weight of catalyst, an organotin compound and ethyl silicate (sold as Catalyst 25X, also from Path Silicones, Elmwood Park, N.J.) was added. The preferred ratio of siloxane to catalyst is 10 to 1. The mixture was poured into a mold containing a rose. The mixture was allowed to set for twenty-fours hours before being removed. The polysiloxane matrix was removed from the mold. The resulting polymer had excellent clarity, the rose was clearly visible inside the polymer, and had excellent structure stability. The polymer remained rigid and did not slump or slide when placed upon a table.

What is claimed is:

1. A method for making a fragranced decorative item encased in an essentially transparent, rigid polymer matrix comprising:
   providing a monomer; a fragrance; and a catalyst suitable for the monomer;
   admixing the monomer, fragrance and a catalyst;
   providing a mold, said mold containing a decorative item;
   providing the fragrance, monomer and catalyst mixture to the mold;
   allowing the catalyst to polymerize the monomer mixture in the mold;
   removing the decorative item from the mold, providing the decorative item encased in a fragrant essential transparent, rigid polymer, wherein the essentially transparent rigid polymer matrix is greater than 50 weight percent of the combination of the decorative item and the fragrant essentially transparent, rigid polymer matrix.

2. The method of claim 1 wherein the polymer is selected from the group consisting of siloxanes, silicones, acrylics, carbonates, and polyesters.

3. The method of claim 2 wherein the polymer is a polysiloxane.

4. The method of claim 3 where the polysiloxane is polydimethylsiloxane.

5. The method of claim 1 wherein the essentially transparent, rigid polymer matrix is greater than 70 weight percent of the combination of the decorative item and the fragrant essentially transparent, rigid polymer matrix.

6. The method of claim 5 wherein the essentially transparent, rigid polymer matrix is greater than 80 weight percent of the combination of the decorative item and the fragrant essentially transparent, rigid polymer matrix.

* * * * *